(12) United States Patent
Peltier

(10) Patent No.: US 8,357,339 B2
(45) Date of Patent: Jan. 22, 2013

(54) DEVICE FOR DECANTATION DEPOSITION OF CELLS ON AN ANALYSIS PLATE

(75) Inventor: Eric Peltier, Clamart (FR)

(73) Assignee: Novacyt, Velizy Villacoublay (FR)

( * ) Notice: Subject to any disclaimer, the term of this patent is extended or adjusted under 35 U.S.C. 154(b) by 167 days.

(21) Appl. No.: 12/663,095

(22) PCT Filed: Jun. 2, 2008

(86) PCT No.: PCT/FR2008/050969
§ 371 (c)(1),
(2), (4) Date: Jan. 25, 2010

(87) PCT Pub. No.: WO2009/000999
PCT Pub. Date: Dec. 31, 2008

(65) Prior Publication Data
US 2010/0178689 A1    Jul. 15, 2010

(30) Foreign Application Priority Data

Jun. 8, 2007 (FR) .................................. 07 55610

(51) Int. Cl.
*B01D 35/00* (2006.01)
*B01D 41/00* (2006.01)
*B01L 3/00* (2006.01)
*B01L 9/00* (2006.01)

(52) U.S. Cl. ......... 422/534; 422/50; 422/68.1; 422/500; 422/501; 422/502; 422/503; 422/504; 422/513; 422/535; 422/561

(58) Field of Classification Search ............... 422/50, 422/68.1, 561, 566, 72, 82, 500–504, 506, 422/513, 534, 535, 549, 550–554
See application file for complete search history.

(56) References Cited

U.S. PATENT DOCUMENTS

| 5,318,749 | A | * | 6/1994 | Eberle ............................ 422/72 |
| 6,627,158 | B1 |  | 9/2003 | Peltier |

FOREIGN PATENT DOCUMENTS

| DE | 84 16 418 | 8/1984 |
| DE | 39 36 093 | 5/1990 |
| EP | 1 045 249 | 10/2000 |

OTHER PUBLICATIONS

DE8416418U1 Machine Translated Version.*
International Search Report dated Dec. 12, 2008, from corresponding PCT application.

* cited by examiner

*Primary Examiner* — Dean Kwak
(74) *Attorney, Agent, or Firm* — Young & Thompson

(57) ABSTRACT

A device includes a reception chamber (5) for a cell suspension having an open bottom (6) extending opposite a cell deposition area (7) of the analysis plate (1), the bottom (6) of the chamber (5) being in fluid communication with an absorption material (14) for cell preservation liquid for absorbing the latter and enabling a homogeneous decantation deposition on the deposition area (7), the absorption material (14) being provided about the cell deposition area (7). The absorption material (14) includes a compressed area (16) extending between the bottom (6) of the reception chamber (5) and the analysis plate (1) about the cell deposition area (7), and a non-compressed area (17) extending about the compressed area (16).

13 Claims, 3 Drawing Sheets

DEVICE FOR DECANTATION DEPOSITION OF CELLS ON AN ANALYSIS PLATE

BACKGROUND OF THE INVENTION

1. Field of the Invention

The present invention relates to a device for decantation deposition of cells on an analysis plate, said cells being contained in a cell suspension comprising a cell preservation liquid and said cells, said suspension being poured into a reception chamber which is placed above the analysis plate and the bottom of which is open and extends opposite a cell deposition area of the analysis plate, the bottom of the chamber being in fluid communication with an absorption material for the preservation liquid in order to absorb the latter gradually and to permit homogeneous decantation deposition of the cells onto the cell deposition area of the analysis plate, the absorption material being disposed about the cell deposition area, and the bottom of the reception chamber being set at a distance from the analysis plate in order to delimit, between it and the analysis plate, a path for fluid communication between the chamber and the absorption material.

The invention also relates to a sheet of absorption material used in such a device.

2. Description of the Related Art

The document EP-1 045 249, for example, describes a deposition device of this type. In this type of decantation deposition device, the cell preservation liquid starts to be absorbed into the absorbent material as soon as the cell suspension reaches the analysis plate. Such an absorption system results in the cells present in the suspension having a tendency to move towards the edge of the deposition area of the analysis plate since they are dragged along by the preservation liquid, if the absorption of the latter is too rapid. Cell deposition is not then homogeneous on the deposition area, thereby causing a problem for the subsequent analysis of the deposit.

In order to remedy this drawback, a deposition device has been proposed in which the absorbent material is lightly pressed by a member for clamping and holding the absorbent material, which, in a first stage, slows down the absorption of the preservation liquid and permits vertical, homogeneous decantation of the cells. In a second stage, the absorbent material is released and the absorption of the preservation liquid is then accelerated. However, such a device requires a long decantation time for the cell suspension and in addition requires handling of the clamping member during decantation, thereby complicating the process of obtaining the cell deposit.

Other deposition devices propose the use of centrifuging to accelerate cell deposition on the analysis plate. The document U.S. Pat. No. 5,318,749 describes such a device for deposition of cells by centrifuging. However, a centrifuging device is complex, bulky, expensive and not very convenient to use. In addition, such a device cannot easily be integrated in an automated line for obtaining cell deposits, owing to the high speed rotation of such a device. Moreover, centrifuging has a tendency to plicate the cells present in the cell suspension since they are crushed on the analysis plate during centrifuging.

SUMMARY OF THE INVENTION

The aim of the invention is to remedy these drawbacks by proposing a device for decantation deposition of cells which does not necessitate handling of the device during decantation and which ensures uniform deposition of the cells in the cell deposition area of the analysis plate.

To this end, the invention relates to a device for decantation deposition of cells of the aforesaid type, in which the absorption material comprises a compressed area, in which the absorption material is compressed, said compressed area extending between the bottom of the reception chamber and the analysis plate about the cell deposition area, and an uncompressed area, in which the absorption material is not compressed, said uncompressed area extending about the compressed area, beyond the bottom of the reception chamber in relation to the cell deposition area.

The compressed area of the absorption material makes it possible to slow down, in a first stage, the absorption of the preservation liquid, thereby permitting homogeneous deposition of the cells in the cell deposition area of the analysis plate. The absorbed preservation liquid then passes into the uncompressed area of the absorption material, thereby enabling acceleration of the absorption process. Uniform cell deposition is thus obtained in a reduced decantation time.

According to other features of the cell deposition device of the invention:
- the bottom of the reception chamber comprises a seal, said seal bearing homogeneously on the surface of the compressed area of the absorption material;
- the absorption material is in the form of a sheet provided with a hole adapted to extend opposite the cell deposition area of the analysis plate, the compressed area forming the edge of said hole;
- the absorption material for the preservation liquid is held in position by clamping between two members associated with means for fixing and clamping one onto the other, one of which members carries the reception chamber for the suspension and the other includes an impression for receiving the analysis plate;
- the reception chamber is removably disposed in an opening of the member carrying the reception chamber, the reception chamber comprising at least one shoulder extending from the bottom of the reception chamber along a part of the wall of the reception chamber, said shoulder being arranged to lock the reception chamber in the opening of the member and to permit the extraction of the reception chamber from the opening when the shoulder is removed from said opening;
- the member carrying the reception chamber has a widening around the opening of the member, said widening extending opposite the bottom of the reception chamber and part of the shoulder;
- the deposition device comprises a plurality of reception chambers placed above a plurality of analysis plates, said reception chambers being firmly connected to one another by means of material bridges;
- the member receiving the reception chambers comprises a plurality of openings, each receiving a reception chamber, the other member comprising a plurality of impressions for receiving analysis plates, the material bridges connecting the reception chambers extending between said members;
- the absorbent material is in the form of a sheet of absorbent paper; and
- the uncompressed area of the absorbent material has a thickness comprised substantially between 0.9 mm and 1.1 mm and the compressed area of the absorbent material has a thickness substantially equal to 0.4 mm.

The invention also relates to a sheet of absorption material intended to be used in a deposition device such as is defined above, said sheet comprising a hole intended to extend opposite a cell deposition area of an analysis plate, said sheet being characterized in that it comprises a compressed area, in which the absorption material is compressed, said compressed area extending about the hole, and an uncompressed area, in which the absorption material is not compressed, said uncompressed area extending about the compressed area.

Other features and advantages of the invention will become clear from the following description, provided solely by way of example and with reference to the appended drawings.

BRIEF DESCRIPTION OF THE DRAWING FIGURES

DETAILED DESCRIPTION OF THE INVENTION

Figure 1:
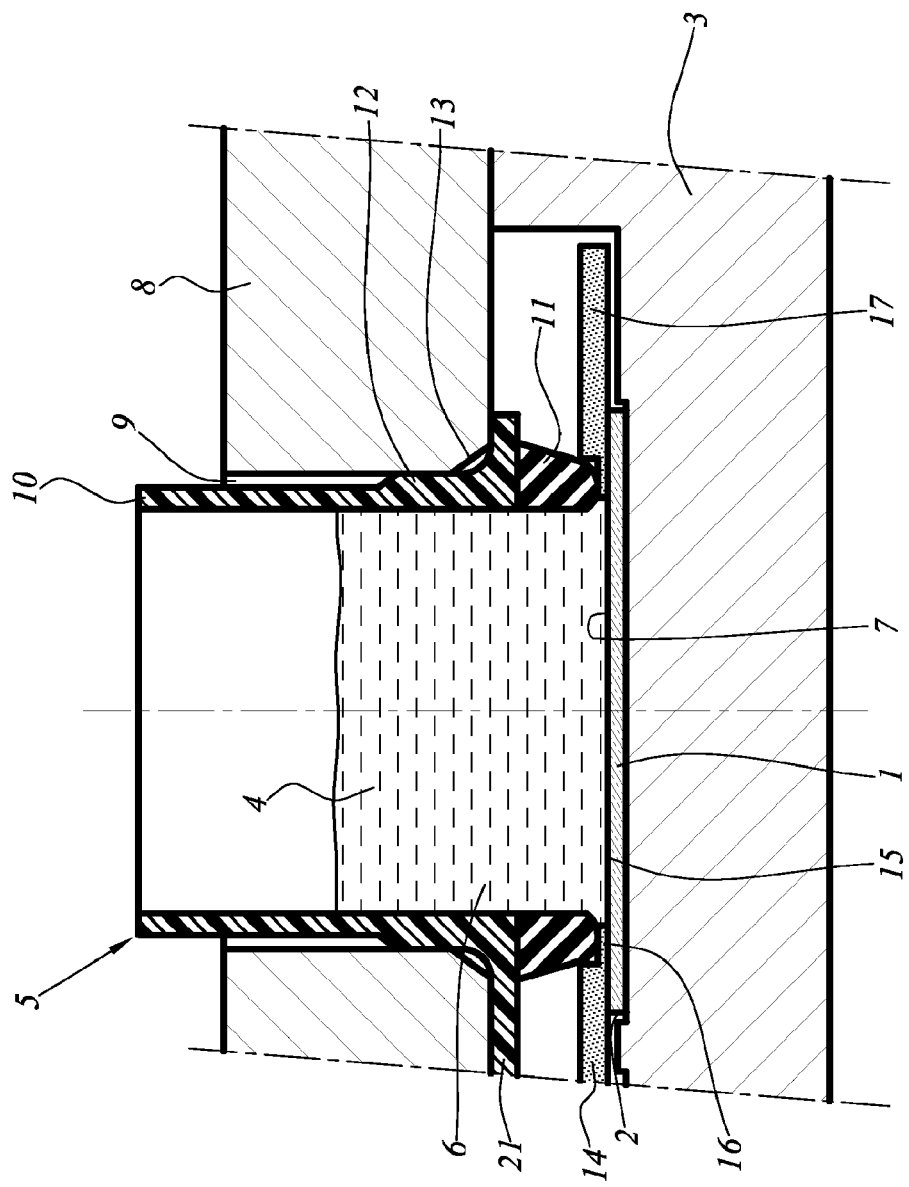
FIG. 1 is a schematic sectional view of an exemplary embodiment of a deposition device according to the invention.

With reference to FIG. 1, a device for decantation deposition of cells on an analysis plate 1 is described. The analysis plate is formed by any suitable plate already known in the prior art.

The plate 1 is received in a corresponding impression 2 of a member 3 forming a base, which will be described in more detail hereinafter.

A cell suspension 4 is poured into a reception chamber 5, placed above the analysis plate 1 and the bottom 6 of which is open and extends opposite a cell deposition area 7 of the analysis plate 1. The cell suspension 4 comprises a cell preservation liquid and the cells which are intended to be collected on the analysis plate 1. The suspension 4 is for example a cervical cytological suspension or a vaginal cytological suspension. It may also be the product of a puncture of a hollow or solid organ, or of an effusion fluid.

The reception chamber 5 is for example carried by a support member 8 comprising an opening 9 into which the reception chamber 5 is inserted. The support member 8 extends opposite the member forming a base 3 and will be described in more detail hereinafter. The reception chamber 5 comprises for example a substantially cylindrical body 10 forming a wall of the reception chamber.

The body 10 comprises at least one shoulder 12 extending from the bottom 6 of the reception chamber along a part of the wall of the reception chamber 5. The shoulder 12 forms a device for locking the reception chamber 5 in the opening 9. That is to say, the reception chamber 5 has a diameter substantially equal to that of the opening 9 in the region of the shoulder 12. According to one embodiment, the body 10 comprises a plurality of shoulders 12, for example four, regularly distributed about the body 10. The diameter of the chamber 5 is then substantially equal to that of the opening 9 in the region of two shoulders disposed opposite each other, as shown in FIG. 1.

The height of the body 10 is such that the reception chamber 5 protrudes out of the opening 9 at the side on which the cell suspension 4 is introduced.

Thus, when cell deposition has been obtained on the analysis plate 1, the support member 8 is withdrawn and the operator pushes on the reception chamber 5 at the side on which the cell suspension 4 is introduced, in order to bring the shoulder 12 out of the opening 9. The chamber 5 is thus released and can come out of the opening 9 at the bottom 6 of the chamber 5 in order to be discarded. Such an embodiment makes it possible to avoid the operator touching the support member or the reception chamber 5 with respect to the bottom of the chamber 5 in order to prevent the risk of contact with any residues of the cell suspension 4 which may be irritant or even corrosive. The operator can also avoid contact with the reception chamber 5 at the side on which the cell suspension 4 is introduced, by turning the support member after obtaining cell deposition and by resting the reception chamber 5 on a surface at the side on which the cell suspension 4 is introduced, so as to bring the shoulder 12 out of the opening 9.

In order to facilitate the withdrawal of the reception chamber 5 from the opening 9, the latter has a widening 13 about the opening 9 extending opposite the bottom 6 of the reception chamber and a part of the shoulder 12, as shown in FIG. 1.

The bottom 6 of the chamber comprises an annular seal 11 disposed beneath the body 10 of the chamber 5. The seal 11 is for example made of a TPE-type material. The seal 11 thus protrudes from the opening 9 at the bottom 6 of the chamber 5.

The seal 11 is set at a distance from the analysis plate 1 so that the reception chamber 5 is in fluid communication with an absorption material 14 for the cell preservation liquid in order to absorb the latter gradually and permit homogeneous deposition of the cells onto the cell deposition area 7 of the analysis plate 1.

The absorption material 14 is for example in the form of a sheet of absorbent paper, provided with a hole 15 adapted to extend opposite the cell deposition area 7 of the analysis plate 1.

The absorption material 14 then extends about the deposition area 7 of the analysis plate 1, between the latter and the reception chamber 5, more precisely between the analysis plate 1 and the seal 11, in order to permit the gradual absorption of the preservation liquid.

The absorption material 14 comprises a compressed area 16 extending between the bottom 6 of the reception chamber 5 and the analysis plate 1 about the cell deposition area 7. By compressed area 16, it is to be understood that the absorption material 14 has been pre-compressed before its use in the cell deposition device and that the area 16 is compressed in relation to the remainder of the absorption material without a particular pressing force being applied to the area 16. The compressed area 16 forms the edge of the hole 15 in the absorption material 14. Thus, when the suspension 4 is placed to decant in the reception chamber 5, the cell preservation liquid is brought into contact with the compressed area 16 of the absorption material. Absorption by this area is slow, owing to the compression of the absorption material, thereby making it possible to allow the cells of the suspension time to be deposited uniformly onto the deposition area 7 of the analysis plate.

The seal 11 and the compressed area 16 are arranged so that the seal 11 bears homogeneously only on the surface of the compressed area 16, as shown in FIG. 1. The seal 11, owing to its resilience, prevents the compressed area 16 from being completely crushed, which would prevent absorption of the cell preservation liquid. The seal also prevents any leakage of cell preservation liquid other than into the absorption material.

According to one embodiment, the compressed area 16 has a thickness substantially equal to 0.4 mm for a thickness of uncompressed absorption material 14 comprised substantially between 0.9 mm and 1.1 mm.

The absorption material 14 further comprises an uncompressed area 17 extending beyond the bottom 6 of the reception chamber 5 relative to the cell deposition area 7. That is to say, the uncompressed area 17 extends about the compressed area 16, as shown in FIG. 1. The uncompressed area 17 extends between the support member 8 and the member forming a base 3, without the support member 8 exerting a pressing force on the uncompressed area 17. As indicated above, the uncompressed area has a thickness comprised substantially between 0.9 mm and 1.1 mm.

The uncompressed area 17 facilitates rapid absorption of the cell preservation liquid, once the latter has passed through the compressed area 16. Thus, absorption takes placed in two stages: a slow absorption phase permitting homogeneous deposition of cells on the deposition area 7, and a rapid absorption phase enabling the decantation time for the cell suspension 4 to be reduced. By way of example, the invention makes it possible to go from a decantation time of around 6 hours to a decantation time of around 15 minutes compared with an embodiment in which the cell suspension would be left to decant in order to obtain homogeneous cell deposition, before being brought into contact with an absorption material to evacuate the preservation liquid after the cells have been deposited.

Figure 2:
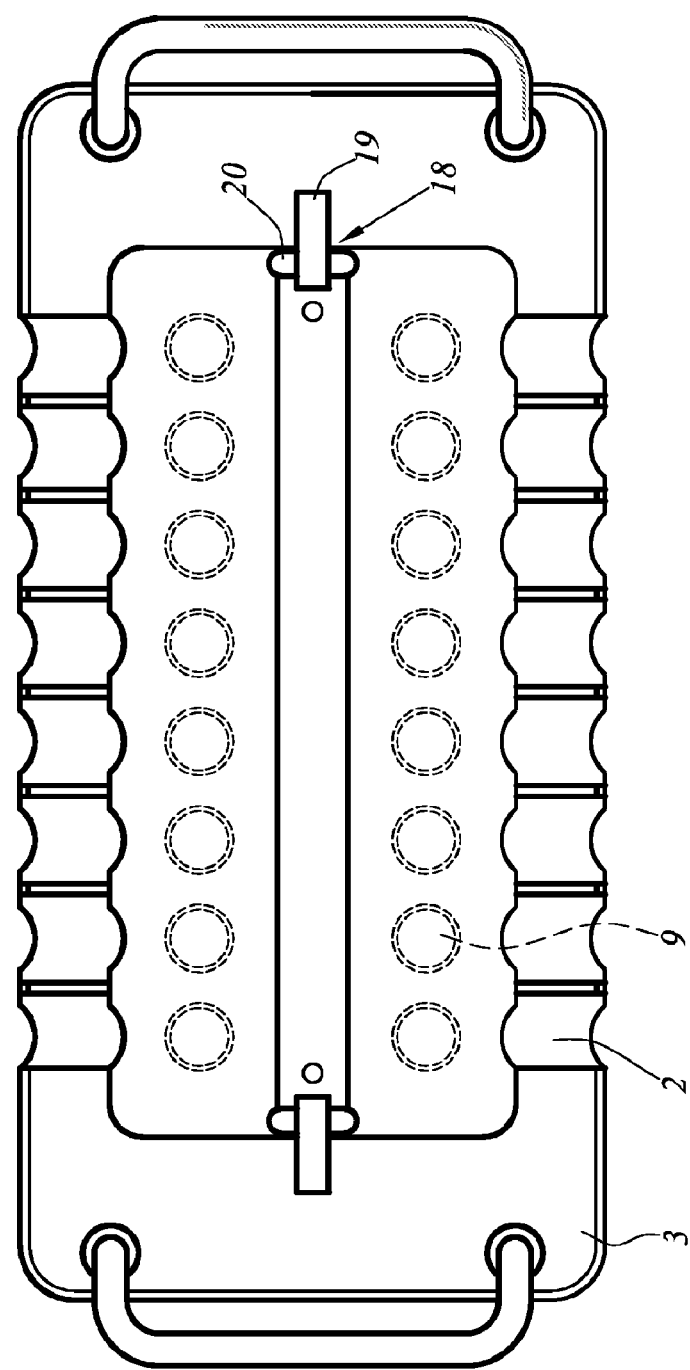
FIG. 2 is a top view of an exemplary embodiment of a deposition device according to the invention.

The support member 8 and member forming a base 3 are fixed and clamped to each other by fixing and clamping means 18, shown in FIG. 2. The means 18 shown in this figure are a hook 19 engaging about a pin 20, but the means 18 could be any other suitable device, such as screws, for example.

The fixing and clamping means 18 are arranged to hold the reception chamber 5 bearing on the absorption material 14 without the seal 11 completely crushing the compressed area 16. The absorption material is thus held in place. In addition, the support member 8 and the member forming a base 3 are arranged so that the analysis plate 1 is disposed perfectly horizontally and completely flat in the region of the deposition area 7 in order to ensure the homogeneous deposition of cells.

Figure 3:
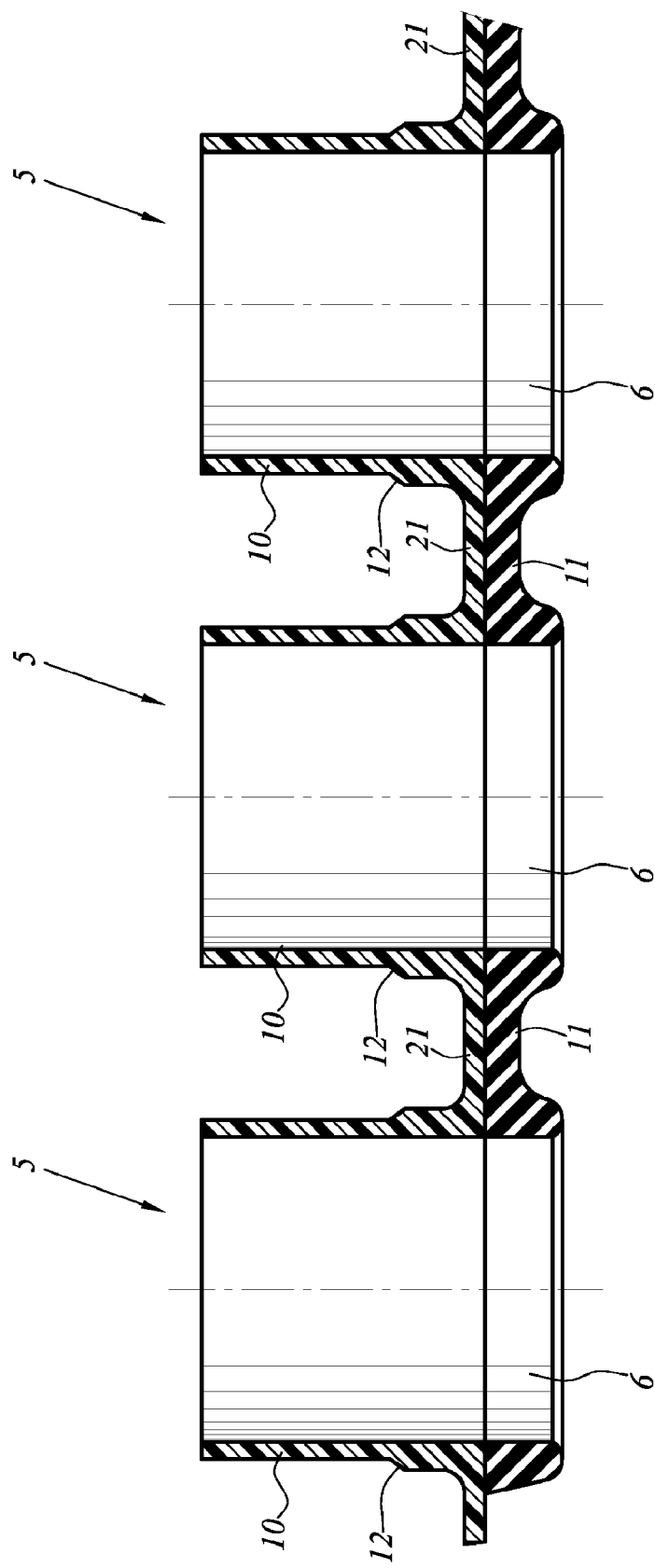
FIG. 3 is a schematic sectional view of reception chambers used in the deposition device of FIG. 2.

According to the embodiment shown in FIG. 2, the support member 8 comprises a plurality of openings 9, each receiving a reception chamber 5. The reception chambers 5 are connected to one another by a material bridge 21, as shown in FIG. 3. The member forming a base 3 comprises a plurality of impressions 2 for receiving analysis plates 1 disposed opposite the openings 9 of the support member 8. The material bridges 21 between the reception chambers 5 extend between the support member 8 and the member forming a base 3 in the region of the bottoms 6 of the reception chambers 5.

The device according to the invention is particularly adapted to the automation of obtaining cell deposits, the support member 8 and member forming a base 3 forming an assembly adapted to functioning with a robot and/or in a cell sample treatment line.

The invention claimed is:

1. A device for decantation deposition of cells on an analysis plate (1), said cells being contained in a cell suspension (4) comprising a cell preservation liquid, said suspension being poured into a reception chamber (5) comprising a body (10) having a wall with an uppermost surface and a lowermost surface, the reception chamber (5) placed above the analysis plate (1) and the bottom (6) of said reception chamber is open and extends opposite a cell deposition area (7) of the analysis plate (1), the bottom (6) of the reception chamber (5) being in fluid communication with a layer of an absorption material means (14) for the preservation liquid in order to absorb the preservation liquid gradually and permit homogeneous decantation deposition of the cells onto the cell deposition area (7) of the analysis plate (1), the absorption material means (14) being disposed about the cell deposition area (7), and the bottom (6) of the reception chamber (5) being set at a distance from the analysis plate (1) in order to delimit, between the reception chamber (5) and the analysis plate (1), a path for fluid communication between the reception chamber (5) and the absorption material means (14), wherein the layer of the absorption material means (14) comprises i) a compressed area (16) of a first material, in which the absorption material (14) is compressed, said compressed area (16) being located between said lowermost surface of said wall of the body and a corresponding upper surface of said analysis plate (1), said compressed area (16) extending between the bottom (6) of the reception chamber (5) and the analysis plate (1) about the cell deposition area (7), and ii) a laterally adjoining uncompressed area (17) of the first material, in which the absorption material means (14) is not compressed relative to said compressed area, said uncompressed area (16) being located extending up from the upper surface of said analysis plate (1) pass the lowermost surface and upward next to said wall of the body, said uncompressed area (17) extending laterally about the compressed area (16), beyond the bottom (6) of the reception chamber (5) in relation to the cell deposition area (7); and wherein the layer of absorption material means (14) in the compressed area (16) exhibits a first density of the first material greater than a second density of the first material in the uncompressed area (17).

2. A deposition device according to claim 1, wherein the bottom (6) of the reception chamber (5) comprises a seal (11), said seal (11) bearing homogeneously on the surface of the compressed area (16) of the absorption material means (14).

3. A deposition device according to claim 2, wherein the absorption material means (14) is in the form of a sheet provided with a hole (15) adapted to extend opposite the cell deposition area (7) of the analysis plate (1), the compressed area (16) forming the edge of said hole (15).

4. A deposition device according to claim 1, wherein the absorption material means (14) is in the form of a sheet provided with a hole (15) adapted to extend opposite the cell deposition area (7) of the analysis plate (1), the compressed area (16) forming the edge of said hole (15).

5. A deposition device according to claim 1, wherein the absorption material means (14) for the preservation liquid is held in position by clamping between two members (3, 8) associated with means (19) for fixing and clamping one onto the other, one of which members carries the reception chamber (5) for the suspension (4) and the other includes an impression (2) for receiving the analysis plate (1).

6. A deposition device according to claim 5, wherein the reception chamber (5) is removably disposed in an opening (9) of the member (8) carrying the reception chamber (5), the reception chamber (5) comprising at least one shoulder (12) extending from the bottom (6) of the reception chamber (5) along a part of the wall of the reception chamber (5), said shoulder (12) being arranged so as to lock the reception chamber (5) in the opening (9) in the member (8) and to permit the extraction of the reception chamber (5) from the opening (9) when the shoulder (12) is removed from said opening (9).

7. A deposition device according to claim 6, wherein the member (8) carrying the reception chamber (5) has a widening (13) around the opening (9) of the member (8), said widening (13) extending opposite the bottom (6) of the reception chamber (5) and a part of the shoulder (12).

8. A deposition device according to claim 6, further comprising a plurality of reception chambers (5) placed above a plurality of analysis plates (1), said reception chambers (5) being firmly connected to one another by means of material bridges (21).

9. A deposition device according to claim 8, wherein the member (8) receiving the reception chambers (5) comprises a plurality of openings (9), each receiving a reception chamber (5), the other member (3) comprising a plurality of impressions (2) for receiving analysis plates (1), the material bridges (21) connecting the reception chambers (5) extending between said members (3, 8).

10. A deposition device according to claim 1, wherein the absorbent material means (14) is in the form of a sheet of absorbent paper.

11. A deposition device according to claim 1, wherein the uncompressed area (17) of the absorbent material means (14) has a thickness comprised substantially between 0.9 mm and 1.1 mm and the compressed area (16) of the absorbent material (14) has a thickness substantially equal to 0.4 mm.

12. A sheet of absorption material means (14) intended to be used in a deposition device according to claim 1, said sheet comprising a hole (15) intended to extend opposite a cell deposition area (7) of an analysis plate (1), said sheet comprising a compressed area (16), in which the absorption material means (14) is compressed, said compressed area extending about the hole (15), and an uncompressed area (17), in which the absorption material means (14) is not compressed, said uncompressed area (17) extending about the compressed area (16).

13. A deposition device according to claim 1, further comprising a plurality of reception chambers (5) placed above a plurality of analysis plates (1), said reception chambers (5) being firmly connected to one another by means of material bridges (21).

* * * * *

UNITED STATES PATENT AND TRADEMARK OFFICE
CERTIFICATE OF CORRECTION

PATENT NO.       : 8,357,339 B2                                      Page 1 of 1
APPLICATION NO.  : 12/663095
DATED            : January 22, 2013
INVENTOR(S)      : Eric Peltier It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 236 days.

Signed and Sealed this

First Day of September, 2015

Michelle K. Lee
*Director of the United States Patent and Trademark Office*